United States Patent [19]

Nodiff

[11] Patent Number: 4,980,360
[45] Date of Patent: Dec. 25, 1990

[54] 5-(PHENYLALKOXY)PRIMAQUINE COMPOUNDS AND THEIR USE FOR TREATMENT OF MALARIA

[75] Inventor: Edward A. Nodiff, Philadelphia, Pa.

[73] Assignee: Calspan Corporation, Buffalo, N.Y.

[21] Appl. No.: 493,038

[22] Filed: Mar. 13, 1990

[51] Int. Cl.$^5$ ..................... A61K 31/47; C07D 215/20
[52] U.S. Cl. ...................................... 514/311; 576/171
[58] Field of Search ........................ 546/171; 514/311

[56] References Cited

U.S. PATENT DOCUMENTS

| | | | |
|---|---|---|---|
| 1,938,047 | 12/1933 | Schonhofer et al. | 260/38 |
| 2,477,479 | 7/1949 | Elderfield et al. | 260/286 |
| 3,948,920 | 4/1976 | Nabih | 260/288 |
| 4,167,638 | 9/1979 | Chen et al. | 546/171 |
| 4,209,519 | 6/1980 | Kinnamon | 424/258 |
| 4,431,807 | 2/1984 | Strube et al. | 546/171 |
| 4,554,279 | 11/1985 | Saggiomo et al. | 514/311 |

*Primary Examiner*—David B. Springer
*Attorney, Agent, or Firm*—Biebel, French & Nauman

[57] ABSTRACT

Improvement in the treatment of malaria has been demonstrated with 5-arylalkoxy primaquine compounds of the formula

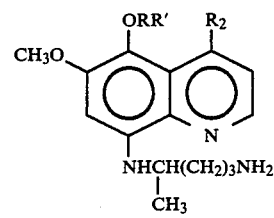

wherein $R_2$ represents H or methyl, R represents an alkylene group having from about 2 to about 12 carbon atoms, R' represents a substituted or non-substituted aryl moiety, such as phenyl and napthyl, and pharmaceutically acceptable salts thereof, wherein the salt forming acid may be organic or inorganic in nature. These primaquine related compounds are effective in malarial chemotherapy, by exerting plasmodicidal activity on malarial parasites present in both the blood and formed tissues of the mammalian host. The 5-arylalkoxy primaquine compounds of the invention are at least as effective in malarial treatment as the prior art 5-alkoxy primaquine compounds, but are not as toxic as the 5-alkoxy compounds at higher dosage ranges.

29 Claims, No Drawings

5-(PHENYLALKOXY)PRIMAQUINE COMPOUNDS AND THEIR USE FOR TREATMENT OF MALARIA

RIGHTS OF U.S. GOVERNMENT

The U.S. Government has a non-exclusive, non-transferable, irrevocable, paid-up license to practice or have practiced this invention for or on its behalf as provided by the terms of contracts Nos. DAMD 17-82-C-2001 and DAMD17-88-C-8106 awarded by the U.S. Department of the Army.

FIELD OF THE INVENTION

The invention relates to a pharmaceutical composition and method of use thereof in treating malaria.

BACKGROUND OF THE INVENTION

Malaria has long presented the most serious of global public health problems among the infectious diseases. Attempts to control the mosquito vector and use of antimalarials notwithstanding, there are yet some one million fatalities annually from the disease. Not clearly evident in the mortality statistics are the vast range of problems related to the tens of millions of cases suffering from morbidity derived from malaria infections. In part, the extent of the economic and public health problems derived from malaria has been related to difficulties in the chemotherapy of that protozoan disease. The narrow spectrum of action of antimalarial drugs in relation to the life cycle of the parasite has been clearly apparent, for example. Development of drug resistance by Plasmodia has further complicated a situation which of necessity includes use of compounds which may be poorly tolerated by many individuals.

Treatment of acute malaria is an urgent medical problem, and may constitute a grave emergency lest there be fatal consequences. Acute malaria is a result of the presence of Plasmodia in the bloodstream, and those parasites must e eradicated to give clinical cure. Malaria resulting from infection with *Plasmodium falciparum* frequently leads to a severe pathophysiologic cascade and death may occur soon after onset of symptoms. Elimination of blood forms of the parasite ordinarily clears the body of *Plasmodium falciparum* (clinical cure of malaria). Infection with *Plasmodium vivax* (and also the rarer parasites, *Plasmodium malariae* and *Plasmodium ovale*, to variable extent) gives rise to a considerable reservoir of tissue forms (exoerythrocytic stage) of the parasite which are able to cause relapses of malaria through intermittent reinvasion of the blood, as, following treatment of the original attack. Thus, alleviation of acute vivax malaria with a (clinical) curative drug does not perforce achieve elimination of all parasites from the body and produce a radical cure. Only when all of the organisms have been cleared form blood and formed tissues can there by freedom from possible relapse of the malaria. Mixed infections in people, as with *Plasmodium falciparum* and *Plasmodium vivax*, require treatment including both clinically curative and radical curative drugs to afford actual eradication of the malaria.

In clinical practice, the management of acute malaria may well follow differing patterns, depending upon the parasite and the severity of the infection. When acquire din regions where falciparum malaria is responsive to chloroquine, that drug or other 4-aminoquinoline may be used in oral treatment of the condition. If the falciparum parasites may be resistant to chloroquine, or if obviously severe infection is presented, treatment may well be by an intravenous infusion of quinine followed by oral administration of mefloquine or of pyrimethamine-sulfadoxine combination. Acute vivax malaria (or, malariae malaria, or ovale malaria) ordinarily responds well to chloroquine treatment. Prevention of relapses due to persistent tissue forms of *Plasmodium vivax* (and, *Plasmodium malariae*, or *Plasmodium ovale*) requires use of a radically curative agent.

Premaquine is one drug that serves as a clinically effective radically curative antimalarial drug. It clears the tissues of malaria parasites (i.e., tissue schizonticide) and also kills sexually differentiated forms (gametocytes) in the blood at clinically usable doses. On the other hand, primaquine is relatively ineffective against the blood schizonts (i.e., little of blood schizonticidal action) which evoke clinical symptoms of malaria. The toxicity of primaquine precludes administration of doses which would be sufficient to treat overt cases of malaria.

It has become apparent that palliative effects of chloroquine are achieved with safe doses of the drug, whereas primaquine may give evidence of toxic effects even at therapeutic doses [cf. World Heath Organization report WHO/MAL/79.905(1979), H. Weniger]. Thus, chloroquine must be administered to scavenge schizonts from the blood while primaquine destroys tissue forms. It appears that the problem with use of primaquine for both effects is two-fold, viz., inadequate blood schizonticidal activity and undue toxicity.

In the course of the U.S. program on antimalarials research during 1941–1945, the serious attempts made to improve the profile of pamaquine led to primaquine. Some investigations of 8-aminoquinolines were continued toward broadening the effectiveness and decreasing the toxicity of primaquine. One approach was to alter the basic side-chain. A representative was 6-methoxy-8-(5-propylaminopentylamino) quinoline phosphate [U.S. Pat. No. 3,096,334 (2July 1963) E.A. Steck; J. Org. Chem., 24, 700(1959) E.A. Steck with L.T. Fletcher], which had sufficiently good profile as a blood- and tissue-schizonticide in the laboratory [Antibiotics Chemother., 12, 103(1962) D.A. Berberian, et al.] that it underwent field trials [e.g., Bull. W.H.O., 32, 591 (1965) R.D. Powell]. It became apparent that such structural modification achieved no appreciable improvement in overall worth of primaquine. Other approaches toward enchancing effectiveness of primaquine included synthesis of 4-methyl primaquine [J. Am. Chem. Soc., 77, 4816(1955), R.D. Elderfield, et al.]. Although previous test systems failed to identify it as superior to primaquine, recent improvements in the evaluation of antimalarials [cf., Am. J. Trop. Med. Hyg., 24, 174(1975), K.E. Kinnamon and W.E. Rothe; ibid., 27, 718 (1978), L.H. Schmidt; ibid., 28, 937(1979), D.S. Rane and K.E. Kinnamon] so indicated. Note may also be taken of the synthesis of 5-substituted 8-aminoquinoline derivatives during the World War II program of antimalarial research in the U.S.A.: cf. The Chemotherapy of Protozoan Diseases, by E.A. Steck (published 1972 by Walter Reed Army Institute of Research, Washington D.C.) - Volume 3, pages 23.160 to 23.162.

PRIOR ART

In U.S. Pat. No. 4,554,279 (Saggiomo et al), it was discovered that certain 5-alkoxyprimaquines were effective against both blood and tissue forms of malaria.

Unfortunately, at higher dosage ranges, the disclosed compounds have demonstrated toxicity.

Similarly, 4-methyl-5-(unsubstituted and substituted phenoxy)-6-methoxy-8-(aminoalkylamino) quinolines are reported in U.S. Pat. No. 4,431,807 (Strube et al) as being effective antimalarial agents demonstrating both tissue schizonticidal (radical curative) and blood schizonticidal (suppressive) activity.

Other patents which may be of interest include 4,209,519 (Kinnamon); 1,938,047 (Schonhofer et al), 2,477,479 (Elderfield et al); and 3,948,920 (Nabih).

SUMMARY OF THE INVENTION

The present invention pertains to 5-phenylalkoxy(5-ORR')primaquine compounds of the formula

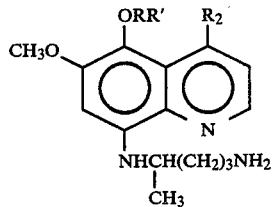

and pharmaceutically acceptable acid addition salts thereof and the use of such compounds to treat both blood and tissue schizonticidal malarial forms. Surprisingly, such compounds demonstrate efficacy that is at least comparable to the well-known 5-alkoxy(5-OR) primaquine analogues per U.S. Pat. No. 4,554,279 (Saggiomo eta al) with the added benefit that the compounds of the present invention are less toxic than the '279 compounds at the upper end of normal dosage ranges.

DETAILED DESCRIPTION OF THE INVENTION

In accordance with the invention, 5-arylalkoxy analogues of primaquine and 4-methylprimaquine are provided and utilized to treat malaria parasites found in the blood, formed tissues or both the blood and formed tissues of warm blooded mammals. The compounds have the structural formula

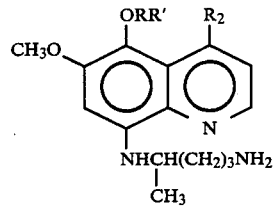

wherein R is an alkylene group having from about 2 to 12 carbon atoms, R' is an aryl moiety such as phenyl and napthyl, or a substituted aryl moiety wherein the substituents are halogen; halogenated $C_1-C_5$ alkyl, such as trifluoromethyl; $C_1-C_5$ alkoxy; and $C_1-C_5$ alkyl. Multiple substituents from the same or different substituent groupings may also be used. $R_2$ is either H or $CH_3$.

In addition to the free base forms of the 5-arylalkoxy(5-ORR')primaquine analogues above shown, the compounds can be administered in the form of pharmaceutically acceptable acid addition salts wherein the salt forming acid may be either organic or inorganic. Nonrestrictive examples of inorganic acids suitable for preparation of salts include: hydrochloric acid; phosphoric acid; nitric acid; sulfamic acid; and sulfuric acid. Suitable organic acids which may be used to form salts include the following, nonrestrictive examples: maleic acid; fumaric acid; succinic acid; citric acid; beta resorcylic acid; and pamoic acid.

The compounds of the invention may be administered either parenterally or perorally to achieve the desired therapeutic effect in the warm blooded mammal in need of such malarial treatment.

When administered in oral dosage forms, subject antimalarial agents may be incorporated into tablets (single or multi-layer, coated or uncoated), capsules, dragees, and the like. The formulation of such oral dosage forms may advantageously include optional excipients such as lactose, precipitated chalk, dibasic calcium phosphate, microcrystalline cellulose derivatives, maize starch, talc, calcium stearate, or like adjuvant substances whose identity and use are well known in pharmaceutical compounding art. For parenteral administration, aqueous or oily solutions of these compounds may be used in a wide range of concentrations. In certain instances, advantages may be gained with use of aqueous suspensions such as may be obtained with ethoxylated sorbitan fatty acid esters, optionally with addition of thickeners such as carboxymethyl cellulose or polyethylene glycol.

Based upon presently available experimental data, compounds preferred for use are the fumaric acid addition salts of 8-(4-amino1-methylbutylamino)-6-methoxy-4-methyl-5-(5-phenylpentoxy)quinoline [R=pentamethylene, R'=phenyl, and $R^2$ =$CH_3$] or 8-(b 4-amino-1-methylbutylamino)-6-methoxy-4-methyl-5-(6-phenylhexoxy)quinoline [R=hexamethylene, R'=phenyl and $R^2=CH_3$].

The novel 5-ORR' primaquine analogues of the invention may e prepared by a five-step reaction scheme proceeding as follows:

Step 1:

A terminally substituted dibromoalkylene compound corresponding in carbon atom number to the desired R substituent is reacted with phenyllithium whereby one of the bromo atoms is replaced by the phenyl moiety to result in a terminally substituted mono bromo, phenyl alkylene compound, such as, for example 1-bromo-7-phenyl-heptane when the desired R and R' substituents for the novel compounds are heptamethylene and phenyl respectively. Note here that when the aryl group is to be a substituted aryl as defined supra., the phenyl or aryl group is provided with the desired substituent(s) at this step.

Step 2:

The bromo and phenyl terminally substituted alkylene from STep 1 (i.e., $BrCH_2(CH_2)_xCH_2R'$) is reacted with 5-hydroxy-6-methoxy-4-methyl-8-nitroquinoline under basic conditions ($Et_3N$+propylene oxide) to result in 6-methoxy-4-methyl-8-nitro-5 ORR'-quinoline. The 5-hydroxy-6-methoxy-4-methyl-8-nitroquinoline reactant for this step is produced in accordance with the disclosure of columns 11 and 12 of U.S. Pat. No. 4,431,807 (Strube et al). The entire disclosure of this patent is incorporated by reference herein.

Step 3:

The nitro group of the 6-methoxy-4-methyl-8-nitro-5 ORR'-quinoline intermediate is reduced to its corresponding amino ($NH_2$) function by reaction with water in the presence of Fe, HOAc, and n-$Bu_2O$ to form 6-methoxy-4-methyl-8-amino-5ORR'-quinoline.

Step 4:

A phthalimide derivative is provided by reacting the amino intermediate with 4-bromo-1phthalimidopentane (BPP) or similar phthalimido compound in the presence of a base such as Et$_3$N.

Step 5:

The phthalimido function is cleaved via hydrazine to form the desired 8-(4-amino-1-methylbutylamino) substituent. If desired, an organic or inorganic salt is reacted with the resulting 8-(4-amino-1-methylbutylamino) containing base compound to form an acid addition salt.

Dosage ranges for the 5-ORR' primaquine compounds of the invention range from about 0.01–1000 mg of the compound or acid addition salt thereof for each kilogram of body weight of the warm blooded mammal.

The invention will now be further described with reference to a number of specific examples which are to be regarded solely as illustrative, and not as restricting the scope of the invention. All temperatures given throughout this disclosure are given in terms of degrees centigrade.

EXAMPLES

Example 1

Preparation of 8-(4-amino-1-methylbutylamino)-6-methoxy-4-methyl-5-(7-phenylheptoxy) quinoline fumarate:

a—Preparation of 1-bromo-7-phenylheptane:

To a stirred solution of 1,7-dibromoheptane (49 g, 0.18 mol) (Aldrich) in THF (300 ml), at −30° C. to −40° C., under N$_2$, was added, dropwise, during 3 h, a solution of phenyllithium (15 g, 0.18 mol) in cyclohexane-ether (2.0 M solution, Aldrich). The reaction was allowed to stir at −10° C. to −20° C. for 3 h and at room temperature overnight. After slow, careful dilution with H$_2$O (50 ml), the aqueous layer was extracted with Et$_2$O (2×150 ml). The extracts and the organic layer were combined, dried (Na$_2$SO$_4$) and concentrated to a yellow oil. Distillation through a Vigreaux column provided 22.5 g of 1-bromo-7-phenylheptane, bp 84°-88° C. (0.2 mm), n$_D^{24}$ 1.5220.

b—Preparation of 6-methoxy-4-methyl-8-nitro-5-(7-phenylheptoxy) quinoline:

To a stirred mixture of 5-hydroxy-6-methoxy-4-methyl-8-nitroquinoline (18 g, 0.077 mol) and 1-bromo-7phenyl heptane [Example 1a](15g, 0.059 mol) in HMPA (45 ml) at 130° C., was added, dropwise, during 1 h, a solution of propylene oxide (18 ml) and Et$_3$N (1 ml). After six more hours, second portions of propylene oxide (4 ml) and Et$_3$N (1 ml) were added and heating was continued for 4 h. The cooled mixture was extracted successively with pet ether, Et$_2$O and Me$_2$CO. The residue returned 2.5 g of starting material (i.e., 5-hydroxy-6-methoxy-4methyl-8-nitroquinoline). The combined pet ether and Et$_2$O extracts were washed (H$_2$O, dil NaOH, H$_2$O) dried (Na$_2$SO$_4$) and concentrated to a viscous oil. This material was dissolved in CHCl$_3$, placed on a silica gel column (200 g) and eluted with CHCl$_3$. Concentration of the eluates and crystallization of the residue from pet ether (Darco) gave 12 g, (50%) of 6-methoxy-4-methyl-8-nitro-5-(7-(phenyl heptoxy) quinoline as yellow crystals, mp 53°-54° C.

Anal. Calcd. for C$_{24}$H$_{28}$N$_2$O$_4$: C, 70.56; H, 6,91; N, 6.86. Found: C, 70.63, H, 6.62; N, 6.81.

c—Preparation of 8-amino-6-methoxy-4-methyl-5-(7-phenyl heptoxy) quinoline:

A stirred mixture of 6-methoxy-4methyl-8-nitro-5-(7-phenylheptoxy) quinoline [Example 1b](2.0 g, 0.005 mol) de-greased 40 mesh Fe filings (5 g) H$_2$O (20 ml), HOAc (4 ml) and n-Bu$_2$O was heated at 80°-85° C. for 1 h, cooled and filtered. The solid was thoroughly extracted with Et$_2$O (500 ml) and the extract was dried (Na$_2$SO$_4$) treated with charcoal and concentrated to an oil. Crystallization from pet ether gave 1.6 g (85%) of 8-amino-6-methoxy-4-methyl-5-(7-phenylheptoxy) quinoline as yellow green crystals, mp 61°-63° C. A second crystallization from pet ether (Darco) provided the analytical sample as glistening yellow crystals, mp 64°-65° C.

Anal. Calcd. for C$_{24}$H$_{30}$N$_2$O$_2$: C, 76.15; H, 7.99; N, 7.40. Found: C, 76.15, H, 7.85; N, 7.21.

d—Preparation of 6-methoxy-4-methyl-8-(1-methyl-4-phthalimidobutylamino)-5-(7-phenylheptoxy) quinoline.

A stirred mixture of 8-amino-6-methoxy-4-methyl-5-(7-phenylheptoxy) quinoline [Example 1c] (9.2 g, 0.024 mol) and 4-bromo-1-phthalimidopentane (BPP) (15 g, 0.05 mol) was heated at 120°-125° C. while Et$_3$N (5 ml) was added in small portions. After 3 h at 120°-125° C., second portions of BPP (7.5g) and Et$_3$N (2.5 ml) were added and heating was continued for 4 h. Third portions of BPP (3 g) and Et$_3$N (1 ml) were introduced, and heating was continued for 2 h. The reaction was allowed to cool and extracted with Et$_2$O (total, ca. 500 ml). The extract was treated with carbon and then with saturated ethereal hydrogen chloride (300 ml). The resulting dark red semi-solid mass was separated and basified with Et$_2$O - Et$_3$N. Concentration of the ethereal solution left 11.5 g (81%) of brown oil which was dissolved in CHCl$_3$, placed on a silica gel column (200 g) and eluted with CHCl$_3$. The first six eluates (75 ml each) were combined and concentrated to give 10.9 grams of 6-methoxy-4-methyl-8-(1-methyl-4-phthalimidobutylamino)-5-(7-phenylheptoxy) quinoline which was used without further purification.

e—Preparation of 8-(4-amino-1-methylbutylamino)-6-methoxy-4methyl-5-(7-phenylheptoxy) quinoline fumarate:

A stirred mixture of 6-methoxy-4-methyl-8-(1-methyl-4-phthalimidobutylamino)-5-(7-phenylheptoxy) quinoline [Example 1d] (10.9 g., 0.018 mol) 95% NH$_2$NH$_2$ (35 ml), EtOH (200 ml) and CHCl$_3$ (100 ml) was heated at 90°-95° C. for 2.5 h, cooled and filtered. The filtrate was evaporated to dryness in vacuo and the residue was extracted with Et$_2$O. The extract was washed with 30% KOH (3×50 ml), with H$_2$O until neutral, dried (Na$_2$SO$_4$), treated with carbon and then with a saturated solution of fumaric acid in Me$_2$CO. The resulting solid was dried and crystallized from Me$_2$CO. The resulting solid was dried and crystallized from Me$_2$CO (Darco) to give 6.8 g (65%) of 8-(4-amino-1-methylbutylamino) 6-methoxy-4-methyl-5-(7-phenylheptoxy) quinoline fumarate as a yellow solid, mp 149°-151° C.

Anal. Calcd. for C$_{33}$H$_{45}$N$_3$O$_6$: C, 68.37; H, 7.82; N, 7.25. Found: C, 68.53; H, 7.65; N, 6.98.

Example 2

Preparation of 8-(4-amino-1-methyl butylamino)-6-methoxy-4-methyl-5-(3-phenylpropoxy) quinoline:

a—Preparation of 6-methoxy-4-methyl-8-nitro-5-(3-phenylpropoxy) quinoline:

A stirred mixture of 5-hydroxy-6-methoxy-4-methyl-8-nitroquinoline (5.86 g, 0.025 mole), 1-bromo-3 phenylpropane (3.98 g, 0.02 mole), and HMPA (15 ml) was heated at 120° C. while a solution of Et₃N (1 ml) and propylene oxide (6 ml) was added dropwise during 0.5 h. The reaction was continued for 3.5 h, cooled and extracted, successively, with pet ether, Et₂O and Me₂CO, leaving one gram of unreacted 5-hydroxy-6-methoxy-4-methyl-8-nitroquinoline. The combined pet ether and Et₂O extracts were washed (H₂O, dil NaOH, H₂O), dried (Na₂SO₂) and concentrated to give crude 6-methoxy-4-methyl-8-nitro-5-(3-phenylpropxy) quinoline as a viscous dark brown oil. Extraction with boiling ligroine (90°–120° C.) (carbon) and concentration of the extract gave 2 g of 6-methoxy-4-methyl-8-nitro-5-(3-phenylpropoxy) quinoline as a yellow solid, mp 100°–102° C., which was used without further purification.

b—Preparation of 8-amino-6-methoxy-4-methyl-5-(3-phenylpropoxy) quinoline:

A stirred mixture of 6-methoxy-4-methyl-8-nitro-5-(3-phenylpropoxy) quinoline (6.3 g., 0.018 mole), Fe filings (16 g), HOAc (12 ml), H₂O (75 ml) and Bu₂O (9 ml) was heated at reflux for 3 h, cooled and filtered. The residue was thoroughly extracted with Et₂O (700 ml) and the extract was dried (Na₂SO₄) and concentrated to give crude 8-amino-6-methoxy-4-methyl-8-nitro-5-(3-phenylproxy)quinoline as an oil. Crystallization from warm pet ether gave 4.2 g of 8-amino-6-methoxy-4-methyl-8-nitro-5-(3-phenyl propoxy)quinoline as a yellow-brown solid, mp 89–91. The analytical sample was obtained from ligroine (90°–120° C.) (carbon) as a yellow solid, mp 91.0°–91.5° C.

Anal. Calcd. for $C_{20}H_{22}N_2O_2$: C, 74.50; H, 6.87; N, 8.69. Found: C, 74.64; H, 7.13; N, 8.39.

c—Preparation of 6-methoxy-4-methyl-8-(1-methyl-4-phthalimidobutylamino)-5-(3-phenylpropoxy) quinoline:

A stirred mixture of 8-amino-6-methoxy-4-methyl-5-(3-phenyl propoxy)quinoline (3.2 g, 0.01 mole) was heated at 120°–125° C. while Et₃N (1 ml) was added in small portions during 0.5 h. After 2 hr, second portions of 4-iodo-1-phthalimidopentane (3.5 g, 0.01 mole) and Et₃N (1 ml) were added in the usual manner. After an additional hour, tlc still showed the presence of 6-methoxy-4-methyl-8-amino-5-(3-phenyl propoxy) quinoline and third portions of the iodopentane (1.7 g) and Et₃N (0.5 ml) were added. The reaction was maintained at 120°–125° C. for one more hour, cooled and thoroughly extracted with ether. The extract was treated with Et₂O-HCl to give the hydrochloride of 6-methoxy-4-methyl-8-(1-methyl-4-phthalimidobutylamino)-5-(3-phenylpropoxy) quinoline as an orange solid. The latter was dissolved in CHCl₃, treated with 5% NaOh, washed with H₂O, dried (Na₂SO₄) and passed through a silica gel column. Concentration of the eluate and solvent removal gave 4.8 of 6-methoxy-4methyl-8-(1-methyl-4-phthalimidobutylamino)-5-(3-phenylpropoxy) quinoline as an oil which was used without further purification.

d—Preparation of 8-(4-Amino-1-methylbutylamino)-6-methoxy-4-methyl-5-(3-phenylpropoxy) quinoline fumarate:

A stirred mixture of 6-methoxy-4-methyl-8-(1-methyl-4-phthalimidobutylamino)-5-(3-phenylpropoxy) quinoline (4.8 g, 0.009 mol), 95% NH₂NH₂ (12 ml), EtOH (60 ml) and CHCl₃ (30 ml) was heated under reflux for 2.5 h, cooled, filtered and concentrated. The resulting pale brown oil was dissolved in Et₂O, washed with 30% KOH and H₂O and dried (Na₂SO₄). The ethereal solution was treated with a saturated solution of fumaric acid in Me₂CO to give 2.2 g of 8-(4-Amino-1-methylbutylamino)-6-methoxy-4-methyl-5-(3-phenylpropoxy) quinoline fumarate, mp 140°–141° C.

Anal. Calcd. for $C_{29}H_{37}N_3O_6$: C, 66.52; H, 7.12; N, 8.03. Found: C, 66.68; H, 7.12; N, 8.05.

Example 3

Preparation of 8-(4-amino-1-methyl butylamino)-6-methoxy-4-methyl-5-(5-phenylpentoxy) quinoline fumarate:

a—Preparation of 6-methoxy-4-methyl-5-(5-phenylpentoxy)-8-nitroquinoline:

A stirred mixture of 5-hydroxy-6-methoxy-4-methyl-8-nitroquinoline (14.4 g, 0.06 mol), 1-bromo 5-phenyl petane (11 g, 0.05 mol) and HMPA (40 ml) was heated at 120°–125° C. while a solution of propylene oxide (15 ml) and Et₃N (2.5 ml) was added dropwise during 1 h. The reaction was continued for 6 h, allowed to cool, and extracted successively with pet ether, Et₂O and Me₂CO leaving 2.7 g of 5-hydroxy-6-methoxy-4-methyl-8-nitroquinoline. On cooling in dry ice-acetone, the pet ether extract gave 1.3 g of 6-methoxy-4-methyl-5-(5-phenylpentoxy)-8-nitroquinoline as a pale yellow solid, mp 47°–50° C. The Et₂O extract was washed with 5% NaOH, then with H₂O, dried (Na₂SO₄) and concentrated. The residual oil was eluted with CHCl₃ from a column of silica gel and the eluate was concentrated. The resulting oil was dissolved in CHCl₃ and again passed through a silica gel column. Solvent removal left an oil which solidified on standing. Trituration of the solid with pet ether provided additional 6-methoxy-4-methyl-5(5-phenylpentoxy)-8-nitroquinoline as yellow solid, mp 47°–50° C.; total yield, 9.1 g (50%). Recrystallization from hexane afforded the analytical sample, mp 53.5°–54° C.

b—Preparation of 8-Amino-6-methoxy-4-methyl-5-(5-phenylpentoxy)quinoline:

A stirred mixture of 6-methoxy-4-methyl-5-(5-phenylpentoxy)-8-nitroquinoline (9.0 g, 0.024 mole), degreased 40 mesh Fe filings (22.5 g), H₂O (90 ml), HOAc (18 ml) and Bu₂O (18 ml) was heated at 80° C. for 1 h, cooled, diluted with H₂O and filtered. The dark solid was thoroughly extracted with warm Et₂O (total, Ca. 500 ml) and the extract was dried (Na₂SO₄), treated with charcoal and concentrated. The resulting dark brown oil was crystallized from pet ether to give 7.3 g (87%) of 8-Amino-6-methoxy-4-methyl-5-(5-phenylpentoxy) quinoline as yellow green crystals, mp 65°–66° C. This material was used without further purification.

c—Preparation of 6-methoxy-4-methyl-8-(1-methyl-4-phthalimidobutylamino)-5-(5-phenylpentoxy) quinoline:

A stirred mixture of 8-Amino-6-methoxy-4-methyl-5-(5-phenylpentoxy)quinoline (4.7 g, 0.013 mole), and 4-bromo-1-phthalimidopentane (BPP) (6.0 g, 0.02 mole) was heated at 125°–130° C. while Et₃N (2 ml) was added in small portions. After 2.5 h at 125°–130 ° C., second portions of BPP (4 g) and Et₃N (1.5 ml) were introduced and heating was continued for 2 h. Third portions were added of BPP (4 g) and Et₃N (1.5 ) and after 2h, fourth portions of BPP(2 g) and Et₃N(1 ml). The reaction was heated for 2 more hours, allowed to cool and extracted with Et₂O. The extract was treated with charcoal and concentrated to a dark brown oil. Solution of the oil in Et₂O (400 ml) and addition of ethereal HCl produced a dark red semi-solid. The latter was separated, basified with ethereal Et₃N and concentrated to a brown oil. This material was passed through a silica gel column, in CHCl$_3$ solution, concentrated and used without further purification.

d—Preparation of 8-(4-amino-1-methylbutylamino)-6-methoxy-4-methyl-5-(5-phenylpentoxy) quinoline fumarate:

A stirred mixture of 6-methoxy-4-methyl-8-(1-methyl-4-phthalimidobutylamino)-5-(5-phenylpentoxy) quinoline (8.0 g, 0.014 mole), 95% NH$_2$NH$_2$ (20 ml), EtOH (120 ml) and CHCl$_3$ (60 ml) was heated at 80° C. for 2 h, cooled, filtered and concentrated in vacuo. The residue was extracted with Et$_2$O and the extract was washed with 30% KOH (3×100 ml) and H$_2$O (until neutral), dried (Na$_2$SO$_4$) and concentrated to an oil. Treatment of a solution of the oil in Me$_2$CO with carbon and then with a saturated solution of fumaric acid in Me$_2$CO (200 ml) gave a yellow solid. Thorough washing with Me$_2$CO provided 5.1 g (65%) of 8-(4-amino-1-methylbutylamino)-6-methoxy-4-methyl-5-(5-phenylpentoxy) quinoline fumarate as a yellow solid, mp 148°-150° C. Recrystallization from Me$_2$CO did not change the melting point.

Anal. Calcd. for C$_{31}$H$_{41}$N$_3$O$_6$: C, 67.49; H, 7.49; N, 7.62. Found: C, 67.25; H, 7.33; N, 7.38.

Example 4

Preparation of 8-(4-amino-1-methylbutylamino)6-methoxy-4-methyl-5-(6-phenylhexoxy) quinoline fumarate:

a—Preparation of 6-methoxy-4-methyl-8-nitro-5-(6-phenylhexoxy) quinoline:

To a stirred mixture of 5-hydroxy-6-methoxy-4-methyl-8-nitroquinoline (2.3 g, 0.01 mole), 1-bromo-6-phenylhexane (2.4 g, 0.01 mole) and HMPA (25 ml), at 130° C., was added dropwise, during 2 h, a mixture of Et$_3$N (1ml) and propylene oxide (9 ml). After four more hours, an additional 10 ml of the Et$_3$N—propylene oxide mixture was introduced. Heating was continued for 24 h and 1.2 g (0.005 mole) of 1-bromo-6-phenylhexane was added followed by another 10 ml of Et$_3$N—propylene oxide. This final mixture was heated for 6 h, allowed to cool, diluted with CHCl$_3$ (50 ml), placed on a silica gel column and eluted with CHCl$_3$. Concentration of the yellow eluate gave 2.3 g of 6-methoxy-4-methyl-8-nitro-5-(6-phenylhexoxy) quinoline as an oil which was used without further purification.

b—Preparation of 8-amino-6-methoxy-4-methyl-5-(6-phenylhexoxy) quinoline hydrochloride:

A vigorously stirred mixture of 6-methoxy-4-methyl-8-nitro-5-(6-phenylhexoxy) quinoline (3.5 g 0.008 mol) Fe filings (5 g), H$_2$O (250 ml), Bu$_2$O (5 ml) and AcOH (1 ml) was heated at 100°-105° C. for 6 hr, allowed to cool and filtered. The filtrate and the residue were extracted with Et$_2$O and the combined extracts were washed with saturated NaCl and dried (Na$_2$SO$_4$). Ethereal hydrogen chloride was added until precipitation was complete and the resulting orange crystals were washed with Et$_2$O; yield, 2.5 g (70%); mp 166°-169° C. Recrystallization from AcOEt (darco) provided the analytical sample as fine orange needles, mp 171°-173° C.

Anal. Calcd. for C$_{23}$H$_{29}$ClN$_2$O$_2$: C, 68.90; H, 7.29; N, 6.99. Found: C, 68.87; H, 7.34; N, 6.70.

The hydrochloride was treated with a mixture of Et$_2$O (200 ml) and 10% Na$_2$CO$_3$ (100 ml) and the extract was washed with saturated NaCl and dried (Na$_2$SO$_4$). Solvent removal left the free base as an orange oil which was used without further purification.

c—Preparation of 6-methoxy-4methyl-8-(1-methyl-4-phthalimidobutylamino)-5-(6-phenylhexoxy) quinoline:

A stirred mixture of 8-amino-6-methoxy-4-methyl-5-(6-phenylhexoxy) quinoline hydrochloride (2.7 g, 0.007 mol), and 4-iodo-1-phthalimido-pentane (IPP) (3.0 g, 0.009 mol) was maintained at 100° C. while 1 ml of Et$_3$N was added dropwise. After an additional 3 h of IPP and 1 ml of Et$_3$N were added, heating was continued for 4 h and the mixture was allowed to cool, diluted with Et$_2$O (100 ml), filtered, washed with saturated NaCl and dried (Na$_2$SO$_4$). Solvent removal provided a quantitative yield of 6-methoxy-4-methyl-8-(1-methyl-4-phthalimidobutylamino)-5 -(6-phenylhexoxy) quinoline as a brown syrup which was used without further purification.

d—Preparation of 8-)4-amino-1-methylbutylamino)-6-methoxy-4-methyl-5-(6-phenylhexoxy) quinoline fumarate:

A stirred mixture of 6-methoxy-4-methyl-8-(1-methyl-4-phthalimidobutylamino)-5-(6-phenylhexoxy) quinoline (11.4 g, 0.02 mole), 95% NH$_2$NH$_2$ (30 ml), CHCl$_3$ (125 ml) and EtOH (500 ml) was heated under reflux for 3.5 h, cooled, filtered and concentrated. The resulting syrup was extracted with Et$_2$(400 ml) and the extract was washed with 30% KOH (2×50 ml) and H$_2$O (10×75 ml), dried Na$_2$SO$_4$), treated with Darco G 60 and filtered. Addition to the filtrate of 1% fumaric acid (300 ml) produced a hygroscopic pale yellow solid which was recrystallized twice from Me$_2$CO containing a small amount of fumaric acid. The crystals were washed with AcOEt and dried in vacuo (6 h at room temp., 4 h at 60°-80° C.) to give 3.1 g of 8-(4-amino-1-methylbutylamino)-6-methoxy-4-methyl-5-(6-phenylhexoxy) quinoline fumarate as yellow crystals, mp 142°-144° C.

Anal. Calcd. for C$_{32}$H$_{43}$N$_3$O$_6$: C, 67.94; H, 7.66; N, 7.43. Found: C, 67.71; H, 7.51; N, 7.15.

Example 5

Preparation of 8-(4-amino-1-methylbutylamino)-6-methoxy-4-methyl-5-(4-phenylbutoxy) quinoline fumarate:

a—Preparation of 6-methoxy-4-methyl-8-nitro-5(4-phenylbutoxy) quinoline:

To a stirred mixture of 5-hydroxy-6methoxy-4-methyl-8-nitroquinoline (5.9 g, 0.025 mol), 1-bromo-4-phenylbutane (4.3 g, 0.02 mol) and HMPA (15 ml), at 110°-115° C., was added dropwise, during 1 h, a mixture of propylene oxide (6 ml) and Et$_3$N (1 ml). The reaction was continued for 5 h, allowed to cool and extracted successively with pet ether, Et$_2$O and Me$_2$CO leaving 1.1 g of insoluble starting material, 5-hydroxy-6-methoxy-4-methyl-8-nitroquinoline. The pet ether and Et$_2$O fractions were worked up as described above for 6-methoxy-4-methyl-8-nitro-5-(7-phenylheptoxy)quinoline (see example 1, part b) to give crude 6-methoxy-4-methyl-8-nitro-5(4-phenylbutoxy) quinoline as an oil. This material was dissolved in CHCl$_3$, placed on a silica gel column and eluted with CHCl$_3$. The eluates were concentrated to an oil which on trituration with pet ether gave 3.2 g (43%) of 6-methoxy-4-methyl-8-nitro-5-(4-phenylbutoxy) quinoline as yellow-green crystals, mp 88°-89° C. Recrystallization from hexane provided the analytical sample, mp 90°-91° C.

Anal. Calcd. for C$_{21}$H$_{22}$N$_2$O$_4$: C. 68.83; H, 6.05; N, 7.65. Found: C. 69.04; H, 6.14; N, 7.38.

b—Preparation of 8-amino-6-methoxy-4-methyl-5-(4-phenylbutoxy)quinoline:

A stirred mixture of 6-methoxy-4-methyl-8nitro-5-(4-phenylbutoxy) quinoline (3.7 g, 0.01 mol), degreased 40mesh Fe filings (10 g), H$_2$O (40 ml), HOAc (8 ml) and Bu$_2$O (8 ml) was heated at 80°–100° C. for 2.5 h, allowed to cool and filtered. The solid was thoroughly extracted with Et$_2$O and the extract was dried (Na$_2$SO$_4$), treated with carbon and concentrated to an oil. Extraction of the latter with pet ether and cooling the extract gave 2.2 g (66%) of 8-amino-6methoxy-4-methyl-5-(4-phenylbutoxy)quinoline as yellow-green crystals, mp 59°–59.5° C. Recrystallization from pet ether afforded the analytical sample as yellow crystals, mp 60°–61° C.

Anal. Calcd. for C$_{21}$H$_{24}$N$_2$O$_2$: C, 74.97; H, 7.19; N, 8.33. Found: C, 74.72; H, 7.09; N, 8.07.

c—Preparation of 6-methoxy-4-methyl-8-(1-methyl-4-phthalimidobutylamino)-5-(4-phenylbutoxy) quinoline:

A stirred mixture of 8-amino-6-methoxy-4-methyl-5-(4-phenylbutoxy)quinoline (12.8 g, 0.038 mol) and 4-bromo-1-phthalimidopentane (BPP) (22.6 g, 0.076 mol) was heated at 135°–140° C. while Et$_3$N (7 ml) was added in small portions during 1 hr. After 1.5 h at 135°–140° C., second portions of BPP (11.3 g) and Et$_3$N (3.5 ml) were added and heating was continued for 2 h. Third portions of BPP (11.3 g) and Et$_3$N (3.5 ml) were introduced and heating was continued for another 2 h. The mixture was allowed to cool and thoroughly extracted with Et$_2$O (total, ca. 600 ml). The extract was treated with charcoal and then with saturated ethereal hydrogen chloride (250 ml). The resulting dark red semi-solid mass was separated by decantation and basified with ethereal Et$_3$N. Concentration of the ethereal solution left a brown oil which was dissolved in CHCl$_3$, placed on a silica gel column (200 g) and eluted with CHCl$_3$. The first fractions were combined on the basis of TLC and concentrated to give 23 g of 6-methoxy-4-methyl-8-(1-methyl-4-phthalimidobutylamino)-5-(4-phenylbutoxy) quinoline as an oil which was used without further purification.

d—Preparation of 8-(4-amino-1-methylbutylamino)-6-methoxy-4-methyl-5-(4-phenylbutoxy) quinoline fumarate:

A stirred mixture of 6-methoxy-4-methyl-8-(1-methyl-4-phthalimidobutylamino)-5-(4-phenylbutoxy) quinoline (23 g, 0.04 mol) 95% NH$_2$NH$_2$ (50 ml), EtOH (300 ml) and CHCl$_3$ (150 ml) was heated at 90°–100° C. for 2 h, cooled and filtered. The filtrate was evaporated to dryness in vacuo and the residue was extracted with Et$_2$O (total, 300 ml). The extract was washed with 30% KOH (3×100 ml), with H$_2$O until neutral, dried (Na$_2$SO$_4$), treated with carbon and then with a saturated solution of fumaric acid in Me$_2$CO. The resulting solid was crystallized from Me$_2$CO to give 8.5 g (40%) of 8-(4-amino-1-methylbutylamino)-6-methoxy-4methyl-5-(4-phenylbutoxy) quinoline fumarate as a yellow solid, mp 145°–147° C.

Anal. Calcd. for C$_{30}$H$_{39}$N$_3$O$_6$: C. 67.02; H, 7.31; N, 7.82. Found: C, 66.94; H, 7.07; N, 7.55.

Example 6

Preparation of 8-(4-amino-1-methylbutylamino)-6-methoxy-4-methyl-5-(8-phenyloctoxy) quinoline fumarate:

a—Preparation of 6-methoxy-4-methyl-8-nitro-5-(8-phenyloctoxy) quinoline:

To a stirred mixture of 5-hydroxy-6-methoxy-4-methyl-8-nitroquinoline (4.98 g, 0.02 mol), 1-bromo-8-phenyloctane (4.7 g, 0.017 mol) and HMPA (13 ml), at 120° C., was added, dropwise, during 1 h, a mixture of propylene oxide (6 ml) and Et$_3$N (1 ml). The reaction was continued for 3.5 h, allowed to cool and extracted successively with pet ether, Et$_2$O and Me$_2$CO leaving 1 g of insoluble starting material, 5-hydroxy-6-methoxy-4methyl-8-nitroquinoline. The combined pet ether and Et$_2$O extracts were washed (H$_2$O, dil NaOH, H$_2$O), dried (Na$_2$SO$_4$) and concentrated. The residue was dissolved in CHCl$_3$, placed on a silica gel column and eluted with CHCl$_3$. Concentration of the eluates left an oil which was triturated with pet ether to give 4.35 g (60%) of 6-methoxy-4-methyl-8-nitro-5-(8-phenyloctoxy) quinoline as yellow solid, mp 39.5°–41° C. Crystallization from hexane (Darco) provided the analytical sample as yellow crystals, mp 41°–42° C.

Anal. Calcd. for C$_{25}$H$_{30}$N$_2$O$_4$: C, 71.06; H, 7.16; N, 6.63. Found: C. 70.66; H, 6.85; N, 6.24.

b—Preparation of 8-amino-6-methoxy-4-methyl-5-(8-phenyloctoxy) quinoline:

A stirred mixture of 6-methoxy-4-methyl-8-nitro-5-(8-phenyloctoxy) quinoline (2.1 g, 0.005 mol), degreased 40 mesh Fe filings (5 g), H$_2$O (20 ml), HOAc (4 ml) and n-Bu$_2$O (4 ml) was heated at 80° C. to 1.5 h, cooled and filtered. The solid was thoroughly extracted with Et$_2$O and the filtered extract was dried (Na$_2$SO$_4$), treated with carbon and concentrated to an oil. Trituration with pet ether gave 1.2 g (61%) of 8-amino-6-methoxy-4-methyl-5-(8-phenyloctoxy) quinoline as yellow-green solid, mp 33°–34° C. Crystallization from pet ether (Darco) gave the analytical sample as yellow green crystals, mp 39°–40° C.

Anal. Calcd. for C$_{25}$H$_{32}$N$_2$O$_2$: C, 76.49; H, 8.22; N, 7.13. Found: C, 76.22; H, 8.17; N, 6.86.

c—Preparation of 6-methoxy-4-methyl-8-(1-methyl-4-phthalimidobutylamino)-5-(8-phenyloctoxy) quinoline:

A stirred mixture of 8-amino-6-methoxy-4-methyl-5-(8-phenyloctoxy) quinoline (5.7 g, 0.014 mol), and BPP (9 g, 0.03 mol) was heated at 120°–135° C. while Et$_3$N (3 ml) was added in small portions during 0.5 h. After 2 h, second portions of BPP (4.5 g) and Et$_3$N (1.5 ml) were introduced. Third and fourth portions of BPP (4.5 g) and Et$_3$N (1.5 ml) were added at 2 H intervals. The reaction mixture was heated for 2 h, after addition was complete, and allowed to cool. The mixture was extracted with Et$_2$O and the extract was treated with carbon and then with ethereal hydrogen chloride. The dark red semi-solid was separated, basified with ethereal Et$_3$N, filtered and concentrated. The resulting dark brown oil was dissolved in CHCl$_3$, placed on a silica gel column (100 g) and eluted with CHCl$_3$. The early eluates were combined (TLC–CHCl$_3$) and concentrated to give 7.9 grams (90%) of 6-methoxy-4-methyl-8-(1-methyl-4-phthalimidobutylamino)-5-(8-phenyloctoxy) quinoline as a pale brown oil which was used without further purification.

d—Preparation of 8-(4-amino-1-methylbutylamino)-6-methoxy-4-methyl-5-(8-phenyloctoxy) quinoline fumarate:

A stirred mixture of 6-methoxy-4-methyl-8-(1-methyl-4-phthalimidobutylamino)-5-(8-phenyloctoxy) quinoline (10.6 g, 0.017 mol), 95% NH$_2$NH$_2$ (20 ml), EtOH (140 ml), and CHCl$_3$ (70 ml) was heated at 80°–90° C. for 2 h, cooled and filtered. The filtrate was evaporated to dryness in vacuo and the residue was extracted with Et$_2$O. The extract was washed with 30% KOH (3×50 ml), with H$_2$O until neutral, dried (Na$_2$SO$_4$), treated with carbon and then with a saturated solution of fumaric acid in Me$_2$CO to give 7 g (68%) of 8-(4-amino-1- methylbutylamino)-6-methoxy-4-methyl-5-(8-phenyloctoxy) quinoline fumarate as yellow solid, mp. 142°-145° C. Crystallization from Me$_2$CO (Darco) afforded the analytical sample as yellow crystals, mp 142°-145° C.

Anal. Calcd. for C$_{34}$H$_{47}$N$_3$O$_6$: C. 68.77; H, 7.98; N, 7.08. Found: C, 68.56; H, 7.85; N, 6.89.

Example 7

Preparation of 8-(4-amino-1-methylbutylamino)-6-methoxy-4-methyl-5-(9-phenylnonoxy) quinoline fumarate:

a—Preparation of 6-methoxy-4-methyl-8-nitro-5-(9-phenylnonoxy) quinoline:

To a stirred mixture of 5-hydroxy-6methoxy-4methyl-8nitroquinoline (4.7 g, 0.02 mol), 1 bromo-9-phenyl-nonane (4.2 g, 0.015 mol) and HMPA (10 ml), at 125-130° C., was added dropwise, during 0.5 h, a mixture of propylene oxide (6 ml) and Et$_3$N (1 ml). The reaction was continued for 6 h, allowed to cool and extracted successively with pet ether, Et$_2$O and Me$_2$CO leaving 1.9 g of insoluble starting material, 5-hydroxy-6-methoxy-4-methyl-8-nitroquinoline. The combined pet ether and Et$_2$O extracts were washed (H$_2$O, dil NaOH, H$_2$O) dried (Na$_2$SO$_4$) and concentrated. The residual oil was dissolved in CHCl$_3$, placed on a silica gel column (100 g) and eluted with CHCl3. The eluates were concentrated, triturated with pet ether and crystallized from Et$_2$O (Darco) to give 2.1 g of 6-methoxy-4-methyl-8-nitro-5-(9-phenylnonoxy) quinoline as yellow crystals, mp 56°-56.5° C. This material was used without further purification.

b—Preparation of 8-amino-6-methoxy-4-methyl-5-(9-phenylnonoxy) quinoline:

A stirred mixture of 6-methoxy-4-methyl-8nitro-5-(9-phenylnonoxy) quinoline (11 g, 0.025 mol), degreased 40 mesh Fe filings (30 g), H$_2$O (100 ml), HOA c (20 ml) and n-Bu$_2$O (20 ml) was heated at 80° C. for 2 h, cooled and filtered. The solid residue and the filtrate were thoroughly extracted with warm Et$_2$O and the combined extracts were dried (Na$_2$SO$_4$), treated with Darco, and concentrated. The resulting solid was dissolved in pet ether (Darco) and cooled in dry ice—Me$_2$CO to give 6.5 g (64) of 8-amino-6-methoxy-4-methyl-5-(9-phenylnonoxy) quinoline as pale yellow crystals, mp 32°-32.5° C.

Anal Calcd. for C$_{26}$H$_{34}$N$_2$O$_2$: C, 76.81; H, 8.43; N, 6.89. Found: C, 76.91; H, 8.29; N, 6.77.

c—Preparation of 6-methoxy-4-methyl-8-(1-methyl-4-phthalimidobutylamino)5-(9-phenylnonoxy) quinoline:

A stirred mixture of 8-amino-6-methoxy-4-methyl-5-(9-phenylnonoxy) quinoline (0.85 g, 0.002 mol) and 4-bromo-1-phthalimidopentane (BPP) (2.4 g, 0.008 mol) was heated at 125°-135° C. while Et$_3$N (1 ml) was added in small portions during 0.5 hr. After 2 h, second portions of BPP (0.6 g) and Et$_3$N (2 drops) were introduced. Identical additions of BPP (0.6 g) and Et$_3$N (2 drops were made three more times at 1 h intervals. The mixture was allowed to cool, extracted with Et$_2$O and the extract was treated with Darco and evaporated to dryness. The residue was redissolved in Et$_2$O (100 ml) and treated with an excess of ethereal hydrogen chloride. The resulting dark red precipitate was separated by decantation, basified with ethereal Et$_3$N and the solvent was evaporated. The residual brown oil was dissolved in CHCl$_3$, placed on a silica gel column (100 g) and eluted with CHCl$_3$. Concentration of the eluate provided 0.9 g (72%) of 6-methoxy-4-methyl-8-(1-methyl-4-phthalimidobutylamino)-5-(9-phenylnonoxy) quinoline as a pale brown oil which was used without further purification.

d—Preparation of 8-(4-amino-1-methylbutylamino)-6-methoxy-4-methyl-5-(9-phenylnonoxy) quinoline fumarate:

A stirred mixture of 6-methoxy-4-methyl-8-(1-methyl-4-phthalimidobutylamino)5-(9-phenylnonoxy) quinoline (12.0 g, 0.019 mol), 95% NH$_2$NH$_2$ (25 ml), EtOH (200 ml) and CHCl$_3$ (100 ml) was heated at 80°-95° C. for 2 h, cooled and filtered. The filtrate was evaporated to dryness in vacuo and the residue was extracted with Et$_2$O. The extract was washed with 30% KOH (3×80 ml), with H$_2$) until neutral, dried (Na$_2$SO$_4$), treated with Darco and evaporated. The resulting oil was dissolved in Me$_2$CO (200 ml), treated with 250 ml of saturated solution of fumaric acid in Me$_2$CO and allowed to stand in the refrigerator over a weekend to give 6.1 g (53%) of 8-(4-amino-1-methylbutylamino)-6-methoxy-4-methyl-5-(9-phenylnonoxy) quinoline fumarate as a yellow solid, mp 141°-145° C. Recrystallization from Me$_2$CO afforded 5.5 g of 8-(4-amino-1-methylbutylamino)-6-methoxy-4-methyl-5-(9-phenylnonoxy) quinoline fumarate, mp 141°-143° C.

Anal. Calcd for C$_{35}$H$_{49}$N$_3$O$_6$: C, 69.16; H, 8.13; N, 6.91. Found: C, 68.99; H, 8.12; N, 7.02.

Efficacy

In order to access the efficacy of the 5-Orr'-8-amino-6-methoxy quinoline compounds of the invention in clinically curative and radically curative antimalarial activity, the following tests were undertaken. The tests compared the performance of the 5-ORR' compounds of the present invention with the 5-OR compounds disclosed in aforementioned U.S Pat. No. 4,554,279. Methods used were as follows:

General

Malaria parasites (plasmodia) are well-known to have complex life cycles: cf. Malaria Parasites and Other Haemosporidia, by P.C.C. Garnham (Blackwell Scientific Publications, Oxford, 1966). For such reason, various procedures have been developed to assess antimalarial effects at specified stages in the life cycle (Kinnamon and Rothe; Schmidt; Rane and Kinnamon, locc, cit.). In the evaluation of compounds developed in instant program, testing was done for blood schizonticidal effects in mice and for tissue schizonticidal action in rhesus monkeys. Each test system had been standardized, so that clear and reproducible definition of effectiveness could be obtained.

Blood Schizonticidal Test (Trophozoite-Induced *Plasmodium berghei* Infection in Mice)

This system is based on comparisons of responses to test compounds by *Plasmodium berghei* KBG 173 malaria in mice as expressed in mean survival times and the mean survival times of untreated controls. Thus, compounds noted as active produce increases in the survival times of the treated animals that are significant when compared with the survival times of untreated controls. Since an established disease is less sensitive to treatment than a disease in the early stages of development, treatment is withheld until the parasitemia is relatively high in order to insure a more reliable assay of activity and the selection of appropriate compounds for intensive pre-clinical studies.

Utilizing young ICR/HA Swiss mice and a standard inoculum of *Plasmodium berghei* KGB 173, it is possible to produce a uniform disease fatal to 100% of untreated animals within 6 to 8 days with a means survival time of 6.2 days. Test animals weigh from 18 to 22 grams but weight variations in any given experimental or control group are confined to 2-3 grams. All animals in any given test are approximately of the same age. Animals on test are housed in metal-topped plastic cages, given a standard laboratory diet and water ad libitum.

Test animals receive an intraperitoneal injection of 0.5 ml of 1:100 dilution of heparinized heart's blood with a minimum of 90% parasitized cells ($4 \times 10^7$ cells), drawn from donor mice infected one week earlier with *Plasmodium berghei*. The donor strain is maintained by weekly passages in separate groups of mice inoculated with a 0.5 ml of 1:500 dilution of heparinized heart's blood.

Test compounds are administered after dissolution or suspension in peanut oil. A single dose is given subcutaneously 72 hours after the mice are infected with *Plasmodium berghei*. At this time a 10-15 percent parasitemia has developed; the disease is well established but has not produced sufficient debility to alter the response of the host to toxic effects of the drug on test. Since treatment is withheld for three days to permit the infection to become well established and death occurs in untreated controls within 6-8 days, it is felt that this system presents a candidate compound with the maximum challenge. In order to check factors such as changes in the infectivity of *Plasmodium berghei* or in the susceptibility of the host or to detect technical errors, a group of infected animals treated with pyrimethamine at dose levels producing definite increases in survival time is included as a positive control in every experiment.

In each experiment test compounds are administered in graded dosages. With highly active compounds, increases in dose levels are usually followed by increases in the survival time of the treated mice. However, if an active drug is toxic for the host, its toxicity may become a limiting factor; continued increases in dose levels also increase the toxic effects and may result in the diminution of survival times. Deaths prior to the sixth day, when untreated controls begin to die, are regarded as nonparasitic and become the basis for toxicity evaluations. Treated animals are kept under observation for 60 days. Survivors at the end of this period of time are considered as cured.

An increase of 100% in mean survival time is considered the minimum effective response for a candidate compound. In calculating means survival time, toxic deaths and 60-day survivors are not included.

RADICAL CURATIVE TEST IN RHESUS MONKEYS

This test is designed to evaluate the tissue schizonticidal (radical curative) activity of test compounds. Well-conditioned Indian rhesus monkeys of either sex weighing 2-4 kg are utilized. *Plasmodium cynomolgi* (Bastianelli strain) sporozoites are prepared by grinding heavily infected Anopheles *balabacensis* salivary glands in 1:1 monkey serum-saline vehicle.

Method:

Monkeys are infected by I.V. injection of $10^6$ freshly isolated *P. cynomolgi* sporozoites on day 0. A rapidly rising parasitemia develops after a 7-9 day prepatent period, and administration of the test drug is initiated when the rising parasite count exceeds 5000 per $mm^3$ (typically day 10-12). Test drugs are administered orally (by nasogastric intubation) once daily for 7 consecutive days in aqueous solution or, if insoluble, in suspension in 0.3% methylcellulose solution. Chloroquine diphosphate (3.1 mg/kg base/kg orally per day) is always administered concurrently with the test drug for 7 days to eliminate blood schizonts. Thus, any tissue schizonticidal activity of the test drug will always be apparent even if it lacks blood schizonticidal activity.

A vehicle control monkey and a positive drug control (primaquine) monkey are included in each group for inoculated monkeys.

Interpretation:

The effect of the test drug is determined by counting blood parasites. Parasite counts are made daily through day 20, and every two days thereafter. Initially, a clearance of blood parasites is observed due to the blood schizonticidal action of chloroquine. If exoerythrocytic parasites ("tissue schizonts") survive the action of the test drug (i.e., if the drug is inactive or incompletely active) there will be a "relapse" of blood parasites. If there is no relapse within 20 days of the initial clearance of parasitemia, parasitemia is followed for an additional 80 days. If there is no relapse within this period, the experiment is terminated and the monkey is considered "cured".

Primaquine diposphate cures 90% of monkeys in this test system when administered at a dose of 1.3 mg/kg per day for 7 days (1.0 mg/kg free base) in combination with chloroquine.

Results are shown in Tables I and II.

TABLE I

COMPARISON OF 5-ALKOXY AND 5-PHENYLALKOXYPRIMAQUINES
BLOOD SCHIZONTICIDAL ANTIMALARIAL ACTIVITY
(*P. BERGHEI*, MOUSE)[a]

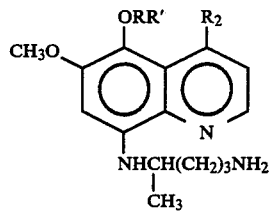

| COMPOUND # | R | R' | Cures(C)[b], Toxic Deaths(T)[c], Δ, MST[d] Dose, mg/kg | | | | | | | |
|---|---|---|---|---|---|---|---|---|---|---|
| | | | 5 | 10 | 20 | 40 | 80 | 160 | 320 | 640 |
| A | $CH_3(CH_2)_2$ | NONE | 1C | 1C | 3C | 3T | | 5T | | 5T |
| 1 | $(CH_2)_3$ | $C_6H_5$ | 1C | 5C | 4C | 4C | 3C | 5T | 5T | 5T |
| B | $CH_3(CH_2)_3$ | NONE | | 11.0 | 5C | 3C | 4T | 5T | 5T | 5T |
| 2 | $(CH_2)_4$ | $C_6H_5$ | 7.6 | 2C | 4C | 4C | 5C | 3C | 0.4 | 0.0 |
| C | $CH_3(CH_2)_4$ | NONE | 5C | 5C | 4C | 1C | 2T | 4T | 5T | 5T |
| 3 | $(CH_2)_5$ | $C_6H_5$ | 7.9 | 3C | 4C | 5C | 5C | 5C | 3C | 1C |
| D | $CH_3(CH_2)_5$ | NONE | 1C | 1C | 5C | 5C | 4C | 3T | 5T | 5T |
| 4 | $(CH_2)_6$ | $C_6H_5$ | 5.9 | 1C | 3C | 4C | 4C | 3C | 3C | 4C |
| E | $CH_3(CH_2)_6$ | NONE | 3C | 3C | 5C | 4C | 2C | 1T | 5T | 5T |
| 5 | $(CH_2)_7$ | $C_6H_5$ | 2C | 5C | 5C | 5C | 5C | 5C | 5C | 5C |
| F | $CH_3(CH_2)_7$ | NONE | 12.0 | 5C | 5C | 5C | 5C | 2C | 0.4 | 2T |
| 6 | $(CH_2)_8$ | $C_6H_5$ | 5.7 | 1C | 2C | 5C | 5C | 5C | 5C | 5C |
| G | $CH_3(CH_2)_8$ | NONE | 9.7 | 2C | 3C | 5C | 5C | 4C | 4C | 4C |
| 7 | $(CH_2)_9$ | $C_6H_5$ | | 1C | 8.5 | 2C | 4C | 5C | 5C | 5C |

[a]Test data were obtained using blood-induced, *P. berghei* infected mice (five animals per group) via the method of Osdene et al. (Osdene, T.S.; Russell, P.B.; J. Rane, L., J. Med. Chem. 1967, 10, 431.)
[b]The number of mice surviving at 60 days post-infection.
[c]Deaths prior to the 6th day.
[d]Increase in mean survival time over controls; a compound is considered active if MST of the treated group is more than twice that of the control group (MST of control group, 6.1 days).

Note that the comparative 5-OR compounds as per U.S. Pat. No. 4,554,279 have been denoted by letters whereas the 5-ORR' compounds of the present invention have been identified by the use of numbers.

TABLE II

COMPARISON OF 5-ALKOXY
AND/5-PHENYLALKOXYPRIMAQUINES
RADICAL CURATIVE ANTIMALARIAL ACTIVITY (DB)
(*P. CYNOMOLGI*, RHESUS)[e]

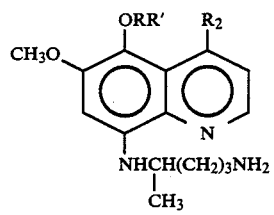

| COMPOUND # | R | R' | Cures/No. of Animals Dose, mg/kg | | | | |
|---|---|---|---|---|---|---|---|
| | | | 0.1 | 0.316 | 1.0 | 0.316 | 10.0 |
| A | $CH_3(CH_2)_2$ | NONE | 0/2 | 2/2 | 1/1 | | |
| 1 | $(CH_2)_3$ | $C_6H_5$ | 1/2 | | 2/2 | | T |
| B | $CH_3(CH_2)_3$ | NONE | 0/2 | 2/2 | 1/1 | | |
| 2 | $(CH_2)_4$ | $C_6H_5$ | 0/3 | 1/2 | 4/4 | | |
| C | $CH_3(CH_2)_4$ | NONE | 3/4 | | 2/2 | | |
| 3 | $(CH_2)_5$ | $C_6H_5$ | 1/2 | 4/4 | 2/2 | | |
| D | $CH_3(CH_2)_5$ | NONE | 5/5 | 3/3 | 1/1 | 0/1 | |
| 4 | $(CH_2)_6$ | $C_6H_5$ | 0/2 | 4/4 | 2/2 | | |
| E | $CH_3(CH_2)_6$ | NONE | 0/2 | 2/2 | 4/4 | | |
| 5 | $(CH_2)_7$ | $C_6H_5$ | 0/2 | 0/4 | 3/3 | | |
| F | $CH_3(CH_2)_7$ | NONE | | 0/1 | 1/1 | | T |
| 6 | $(CH_2)_8$ | $C_6H_5$ | | | | | |
| G | $CH_3(CH_2)_8$ | NONE | 0/2 | 0/2 | 1/1 | T | |

TABLE II-continued

COMPARISON OF 5-ALKOXY
AND/5-PHENYLALKOXYPRIMAQUINES
RADICAL CURATIVE ANTIMALARIAL ACTIVITY (DB)
(*P. CYNOMOLGI*, RHESUS)[e]

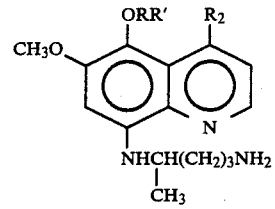

| COMPOUND # | R | R' | Cures/No. of Animals Dose, mg/kg | | | | |
|---|---|---|---|---|---|---|---|
| | | | 0.1 | 0.316 | 1.0 | 0.316 | 10.0 |
| 7 | $(CH_2)_9$ | $C_6H_5$ | | 0/3 | 0/2 | 2/2 | |

[e]Tests were carried out using sporozoite-induced *P. cynomolgi* infected rhesus monkeys according to the procedure of Schmidt et al. (Schmidt, L.N.; Rossan, R.N.; Fradkin, R.; Woods, J. Buli. W.H.O. 1966, 34, 783).

As in Table I, letters were given to the 5-OR compounds of U.S. Pat. No. 4,554,279 with numbers used to identify the 5-ORR' compounds of the invention.

DISCUSSION OF RESULTS AND OPINION THEREON

As can be seen especially in Table I, the 5-ORR' primaquine compounds demonstrated blood schizontical activity which is at the very least comparable to the 5-OR compounds. However as shown by compounds 1–5 especially, the 5-ORR' compounds provided significant toxicity improvement over the analogous 5-OR compounds at dosages of 80mg/kg and greater.

While I have shown and described herein certain embodiments of the present invention, it is intended that there be covered as well any change or modification therein which may be made without departing from the spirit and scope of the invention as defined in the appended claims.

I claim:

1. A compound of the formula

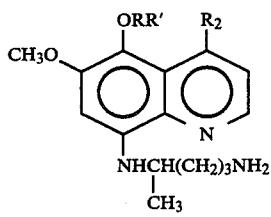

wherein $R_2$ represents H or methyl, R represents an alkylene group having from about 2 to 12 carbon atoms, R' represents a substituted or non-substituted aryl moiety; and pharmaceutically acceptable acid addition salts thereof wherein the salt forming acid is selected from the group consisting of hydrochloric acid, phosphoric acid, nitric acid, sulfamic acid, sulfuric acid, maleic acid, fumaric acid, succinic acid, citric acid, beta-resorcylic acid and pamoic acid.

2. The compound of claim 1 wherein $R_2$ is methyl.
3. The compound of claim 1 wherein $R_2$ is hydrogen.
4. The compound of claim 1 wherein R is a straight chain alkylene group having from about 4 to 8 carbon atoms and wherein R' is phenyl.
5. The compound of claim 4 wherein R has 5 carbon atoms.
6. The compound of claim 4 wherein R has 6 carbon atoms.
7. The compound of claim 5 wherein said salt forming acid is fumaric acid.
8. The compound of claim 6 wherein said salt forming acid is fumaric acid.
9. The compound of claim 1 wherein R has 3 carbon atoms.
10. The compound of claim 4 wherein R has 4 carbon atoms.
11. The compound of claim 4 wherein R has 7 carbon atoms.
12. The compound of claim 4 wherein R has 8 carbon atoms.
13. The compound of claim 1 wherein R has 9 carbon atoms.
14. A method for treating malaria caused by the presence of malaria parasites in the blood, formed tissues, or blood and formed tissues which comprises the step of administering parenterally or orally to an infected animal an antimalarial effective amount of a compound having the formula:

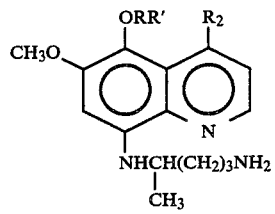

wherein $R_2$ represents H or methyl, R represents an alkylene group having from about 2 to 12 carbon atoms, R' represents a substituted or non-substituted aryl moiety; and pharmaceutically acceptable acid addition salts thereof wherein the salt forming acid is selected from the group consisting of hydrochloric acid, phosphoric acid, nitric acid, sulfamic acid, sulfuric acid, maleic acid, fumaric acid, succinic acid, citric acid, beta-resorcylic acid and pamoic acid.

15. The method of claim 14 wherein R is a straight chain alkylene group having from about 4 to 8 carbon atoms and wherein R is phenyl.
16. The method of claim 14 wherein R has 5 carbon atoms.
17. The method of claim 14 wherein R has 6 carbon atoms.
18. The method of claim 16 wherein said salt forming acid is fumaric acid.
19. The method of claim 17 wherein said salt forming acid is fumaric acid.
20. The method of claim 14 wherein R has 3 carbon atoms.
21. The method of claim 15 wherein R has 4 carbon atoms.
22. The method of claim 15 wherein R has 7 carbon atoms.
23. The method of claim 15 wherein R has 8 carbon atoms.
24. The method of claim 14 wherein R has 9 carbon atoms.
25. The method of claim 14 wherein said animal is a warm blooded mammal.
26. A method for treating malaria caused by the presence of malaria parasites in the blood, formed tissues, or blood and formed tissues which comprises the step of administering orally to an infected animal an antimalarial effective amount of a compound having the formula:

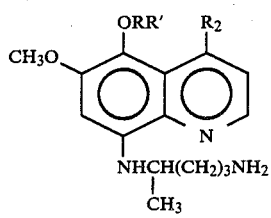

wherein $R_2$ represents H or methyl, R represents an alkylene group having from about 2 to 12 carbon atoms, R' represents a substituted or non-substituted aryl moiety; and pharmaceutically acceptable acid addition salts thereof wherein the slat forming acid is selected from the group consisting of hydrochloric acid, phosphoric acid, nitric acid, sulfamic acid, sulfuric acid, maleic acid, fumaric acid, succinic acid, citric acid, beta-resorcylic acid and pamoic acid, said compound being admixed with an excipient selected from the group consisting of lactose, precipitated chalk, dibasic calcium phosphate, microcrystalline cellulose derivatives, maize starch, talc and calcium stearate.

27. A method as recited in claim 26 wherein said animal is a warm-blooded mammal.

28. A method for treating malaria caused by the presence of malaria parasites in the blood, formed tissues, or blood and formed tissues which comprises the step of:

administering parenterally to an infected animal an antimalarial effective amount of a compound having the formula:

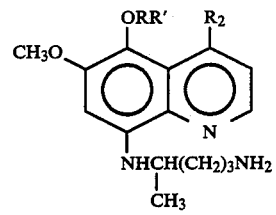

wherein $R_2$ represents hydrogen or methyl; R represents an alkylene group having from about 2 to 12 carbon atoms, R' represents a substituted or non-substituted aryl moiety, and pharmaceutically acceptable salts thereof wherein the salt forming acid is selected from the group consisting of hydrochloric acid, phosphoric acid, nitric acid, fumaric acid, succinic acid, citric acid, beta-resorcylic acid, and pamoic acid, said compound being admixed with an aqueous solution of an ethoxylated sorbitan fatty acid ester.

29. The method of claim 28 wherein the aqueous solution contains a thickener selected from the group consisting of carboxymethyl cellulose and polyethylene glycol.

* * * * *